(12) United States Patent
Li et al.

(10) Patent No.: US 11,986,331 B2
(45) Date of Patent: May 21, 2024

(54) FLAT PANEL DETECTOR AND IMAGING SYSTEM

(71) Applicants: BEIJING BOE SENSOR TECHNOLOGY CO., LTD., Beijing (CN); BOE TECHNOLOGY GROUP CO., LTD., Beijing (CN)

(72) Inventors: Jinyu Li, Beijing (CN); Xuecheng Hou, Beijing (CN)

(73) Assignees: BEIJING BOE SENSOR TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 147 days.

(21) Appl. No.: 17/790,268

(22) PCT Filed: Jun. 11, 2021

(86) PCT No.: PCT/CN2021/099751
§ 371 (c)(1),
(2) Date: Jun. 30, 2022

(87) PCT Pub. No.: WO2022/022110
PCT Pub. Date: Feb. 3, 2022

(65) Prior Publication Data
US 2023/0041531 A1 Feb. 9, 2023

(30) Foreign Application Priority Data
Jul. 29, 2020 (CN) .......................... 202010747055.4

(51) Int. Cl.
*A61B 6/42* (2024.01)
*A61B 6/02* (2006.01)
*H01L 27/146* (2006.01)

(52) U.S. Cl.
CPC .............. *A61B 6/4208* (2013.01); *A61B 6/02* (2013.01); *H01L 27/14663* (2013.01)

(58) Field of Classification Search
CPC ....... A61B 6/4208; A61B 6/02; A61B 6/4233; H01L 27/14663; H01L 27/146;
(Continued)

(56) References Cited

U.S. PATENT DOCUMENTS

| | | | | |
|---|---|---|---|---|
| 4,497,024 A | * | 1/1985 | Roth | ...................... G01T 1/1647 250/363.02 |
| 4,905,265 A | * | 2/1990 | Cox | ....................... G01T 1/2928 378/19 |

(Continued)

*Primary Examiner* — Kiho Kim
(74) *Attorney, Agent, or Firm* — Dilworth & Barrese, LLP.; Michael J. Musella, Esq.

(57) ABSTRACT

A flat panel detector and an imaging system are provided. The flat panel detector includes a plurality of pixel units which include photosensitive pixel units and alignment pixel units. Each photosensitive pixel unit includes a photoelectric sensor configured to convert an incident light into an electrical signal so that a photosensitive pixel unit in which the photoelectric sensor is located has a grayscale that changes according to a real-time change of the incident light. Each alignment pixel unit is configured to have a fixed grayscale, and the fixed grayscale does not change according to the real-time change of the incident light. The alignment pixel units includes first alignment pixel units and second alignment pixel units. Each first alignment pixel unit has a first fixed grayscale, each second alignment pixel unit has a second fixed grayscale different from the first fixed grayscale.

20 Claims, 11 Drawing Sheets

(58) Field of Classification Search
CPC ......... H01L 27/14603; H01L 27/14605; H01L 27/14609; H01L 27/1461; G01N 23/04; G06T 7/13; G09G 3/20
See application file for complete search history.

(56) References Cited

U.S. PATENT DOCUMENTS

| | | | |
|---|---|---|---|
| 2002/0153491 A1* | 10/2002 | Sugawara | G01T 1/2928 250/370.09 |
| 2004/0116795 A1* | 6/2004 | Collins | A61N 5/1048 600/407 |
| 2009/0039277 A1* | 2/2009 | Iwakiri | G01T 1/247 250/370.09 |

* cited by examiner

C-C'

FLAT PANEL DETECTOR AND IMAGING SYSTEM

This present application claims the priority to Chinese patent application No. 202010747055.4, filed on Jul. 29, 2020, the entire disclosure of which is incorporated herein by reference as part of the present application.

TECHNICAL FIELD

At least one embodiment of the present disclosure relates to a flat panel detector and an imaging system.

BACKGROUND

Amorphous silicon (a-Si) X-ray flat panel detector is an X-ray image detector with an amorphous silicon photodiode array as the core component. The scintillator layer or phosphor layer of the detector converts X-ray photons into visible light upon being irradiated by X-ray, then the visible light is converted into an image electrical signal by an amorphous silicon array with the function of a photodiode, and the image electrical signal is transmitted and undergoes an analog-to-digital conversion by peripheral circuits to obtain a digital image. Because the detector needs to go through an imaging process from X-ray to visible light to charge image and then to digital image, the detector is also commonly referred to as a flat panel detector of an indirect-conversion type. The amorphous silicon X-ray flat panel detector has the advantages of fast imaging speed, good spatial and density resolution, high signal-to-noise ratio, and direct digital output, so it is widely used in various digital X-ray imaging devices.

SUMMARY

At least one embodiment of the present disclosure provides a flat panel detector. The flat panel detector comprises a plurality of pixel units arranged in array; the plurality of pixel units comprises: a plurality of photosensitive pixel units and a plurality of alignment pixel units. Each of the plurality of photosensitive pixel units comprises a photoelectric sensor, and the photoelectric sensor is configured to convert an incident light into an electrical signal so that a photosensitive pixel unit in which the photoelectric sensor is located has a grayscale that changes according to a real-time change of the incident light; and each of the plurality of alignment pixel units is configured to have a fixed grayscale, and the fixed grayscale does not change according to the real-time change of the incident light. The plurality of alignment pixel units comprise a plurality of first alignment pixel units and a plurality of second alignment pixel units. Each of the plurality of first alignment pixel units has a first fixed grayscale; each of the plurality of second alignment pixel units has a second fixed grayscale, and the first fixed grayscale is different from the second fixed grayscale.

For example, in the flat panel detector provided by at least one embodiment of the disclosure, an absolute value of a difference between the first fixed grayscale and the second fixed grayscale is greater than or equal to 30% of an absolute value of a difference between a maximum grayscale and a minimum grayscale of the plurality of photosensitive pixel units.

For example, in the flat panel detector provided by at least one embodiment of the disclosure, each of the plurality of first alignment pixel units is a normally black pixel unit, and each of the plurality of second alignment pixel units is a normally white pixel unit.

For example, in the flat panel detector provided by at least one embodiment of the disclosure, at least two first alignment pixel units of the plurality of first alignment pixel units constitute a first alignment mark, and at least two second alignment pixel units of the plurality of second alignment pixel units constitute a second alignment mark.

For example, in the flat panel detector provided by at least one embodiment of the disclosure, the first alignment mark and the second alignment mark are alternately arranged.

For example, in the flat panel detector provided by at least one embodiment of the disclosure, two first alignment pixel units of the plurality of first alignment pixel units constitute the first alignment mark, and the two first alignment pixel units located in the same first alignment mark are respectively located in adjacent columns and adjacent rows of the plurality of pixel units arranged in array; and two second alignment pixel units of the plurality of second alignment pixel units constitute the second alignment mark, and the two second alignment pixel units located in the same second alignment mark are respectively located in adjacent columns and adjacent rows of the plurality of pixel units arranged in array.

For example, in the flat panel detector provided by at least one embodiment of the disclosure, a total number of the at least two first alignment pixel units comprised in the first alignment mark is greater than a total number of the at least two second alignment pixel units comprised in the second alignment mark.

For example, in the flat panel detector provided by at least one embodiment of the disclosure, m*n first alignment pixel units of the plurality of first alignment pixel units constitute the first alignment mark; and two second alignment pixel units of the plurality of second alignment pixel units constitute the second alignment mark, the two second alignment pixel units located in the same second alignment mark are respectively located in adjacent columns and adjacent rows of the plurality of pixel units arranged in array, and m and n are both positive integers.

For example, in the flat panel detector provided by at least one embodiment of the disclosure, m=2, n=8.

For example, the flat panel detector provided by at least one embodiment of the disclosure comprises an image acquisition region. The image acquisition region is configured for acquiring image information and comprises at least part of photosensitive pixel units of the plurality of photosensitive pixel units; and the first alignment mark and the second alignment mark surround the image acquisition region.

For example, in the flat panel detector provided by at least one embodiment of the disclosure, a plurality of the first alignment marks and a plurality of the second alignment marks are evenly distributed in a circumferential direction of the image acquisition region.

For example, in the flat panel detector provided by at least one embodiment of the disclosure, the photoelectric sensor comprises a first electrode, a photoelectric sensing layer and a second electrode. The photoelectric sensing layer is stacked with the first electrode and configured to convert the incident light into the electrical signal, the electrical signal is configured to control a real-time grayscale of the photosensitive pixel unit corresponding to the photoelectric sensor. The second electrode is located on a side of the photoelectric sensing layer away from the first electrode. Each of the plurality of photosensitive pixel units and each of the plurality of alignment pixel units respectively comprise a transistor, comprising a gate electrode, a first electrode and a second electrode. The flat panel detector further comprises signal lines, and the signal lines comprise a bias voltage line, a gate line and a data line. The bias voltage line is electrically connected with the second electrode of the photoelectric sensor and configured to provide a bias voltage to each of the plurality of photosensitive pixel units. The gate line is configured to provide a gate driving signal to the transistor. The data line intersects the gate line to define the plurality of pixel units arranged in array. In each of the plurality of photosensitive pixel units, the first electrode of the transistor is electrically connected with the first electrode of the photoelectric sensor, and the data line is electrically connected with the second electrode of the transistor to read the electrical signal generated by the photoelectric sensing layer.

For example, in the flat panel detector provided by at least one embodiment of the disclosure, each of the plurality of first alignment pixel units also comprises the photoelectric sensor, the transistor of each of at least part of first alignment pixel units of the plurality of first alignment pixel units and the signal lines constitute an open circuit, so that the data line is incapable of reading the electrical signal generated by the photoelectric sensing layer and the at least part of first alignment pixel units are normally black pixel units.

For example, in the flat panel detector provided by at least one embodiment of the disclosure, the gate electrode of the transistor of each of the plurality of first alignment pixel units is disconnected from the gate line.

For example, in the flat panel detector provided by at least one embodiment of the disclosure, the second electrode of the transistor each of the plurality of first alignment pixel units is disconnected from the data line.

For example, in the flat panel detector provided by at least one embodiment of the disclosure, the first electrode of the transistor of each of the plurality of first alignment pixel units is disconnected from the first electrode of the photoelectric sensor.

For example, in the flat panel detector provided by at least one embodiment of the disclosure, at least part of second alignment pixel units of the plurality of second alignment pixel units each also comprise the photoelectric sensor; the second electrode and the photoelectric sensing layer of the photoelectric sensor of each of the at least part of second alignment pixel units respectively have a hollow region, and the hollow region exposes the first electrode of the photoelectric sensor; and the bias voltage line is electrically connected with the first electrode of the photoelectric sensor through a first via hole, the first via hole exposes the first electrode of the photoelectric sensor, the first via hole is located in the hollow region, and the at least part of second alignment pixel units are normally white pixel units.

For example, in the flat panel detector provided by at least one embodiment of the disclosure, at least part of second alignment pixel units of the plurality of second alignment pixel units each comprise a third electrode and a fourth electrode and does not comprise the photoelectric sensing layer; the third electrode is electrically connected with the first electrode of the transistor of the second alignment pixel unit, and the fourth electrode is electrically connected with the bias voltage line; and the third electrode and the fourth electrode are stacked and in direct contact with each other so as to be electrically connected with each other, and the at least part of second alignment pixel units are normally white pixel units.

For example, in the flat panel detector provided by at least one embodiment of the disclosure, the photoelectric sensor is a photodiode.

For example, in the flat panel detector provided by at least one embodiment of the disclosure, the flat panel detector comprises an image acquisition region, and the plurality of photosensitive pixel units generate a charge image according to the electrical signal. The flat panel detector further comprises: a coordinate acquisition unit, configured to acquire coordinates of the plurality of alignment pixel units and real-time coordinates of at least part of the photosensitive pixel units for forming the charge image; and a data output unit, configured to output the electrical signal of each of the plurality of photosensitive pixel units for forming an image, and configured to output the coordinates of the plurality of alignment pixel units and the real-time coordinates of the at least part of the photosensitive pixel units for positioning the charge image so as to control the charge image to always be located in the image acquisition region.

At least one embodiment of the disclosure provides an imaging system. The imaging system comprises any one of the flat panel detectors as described above, a position controller unit, a position adjuster device and an imaging processor module. The position controller unit is configured to receive the coordinates of the plurality of alignment pixel units and the real-time coordinates of the at least part of the photosensitive pixel units in real time, calculate a distance of the at least part of the photosensitive pixel units relative to the plurality of alignment pixel units by using coordinates that are received, and send an instruction according to a calculation result. The position adjuster device is configured to receive the instruction from the position controller unit in real time, and adjust a position of the flat panel detector in real time under control of the instruction so that the charge image is always located in the image acquisition region. The imaging processor module comprises a display and an imaging processor, the display comprises a preset display region, and the imaging processor is configured to receive the electrical signal output by the flat panel detector and position information of the charge image after adjusting the position of the flat panel detector, and generate an image of an object to be imaged in the preset display region by using the electrical signal and the position information of the charge image.

For example, the imaging system provided by at least one embodiment of the disclosure further comprises a light emitter, configured to emit light to the object to be imaged. The light irradiates the flat panel detector after passing through the object to be imaged.

For example, in the imaging system provided by at least one embodiment of the disclosure, the light emitter is further configured to rotate around the object to be imaged, and emit light to the object to be imaged at multiple angles to generate corresponding charge images at each angle in real time, and the imaging processor module is configured to generate a three-dimensional image in the preset display region by processing a plurality of the charge images generated by emitting light to the object to be imaged at multiple angles.

For example, in the imaging system provided by at least one embodiment of the disclosure, the light emitter emits X-ray.

BRIEF DESCRIPTION OF THE DRAWINGS

In order to clearly illustrate the technical solution of the embodiments of the present disclosure, the drawings of the embodiments will be briefly described. It is obvious that the described drawings in the following are only related to some embodiments of the present disclosure and thus are not limitative of the present disclosure.

FIG. 1A is a schematic view of a flat panel detector provided by at least one embodiment of the present disclosure.

DETAILED DESCRIPTION

Figure 1A:
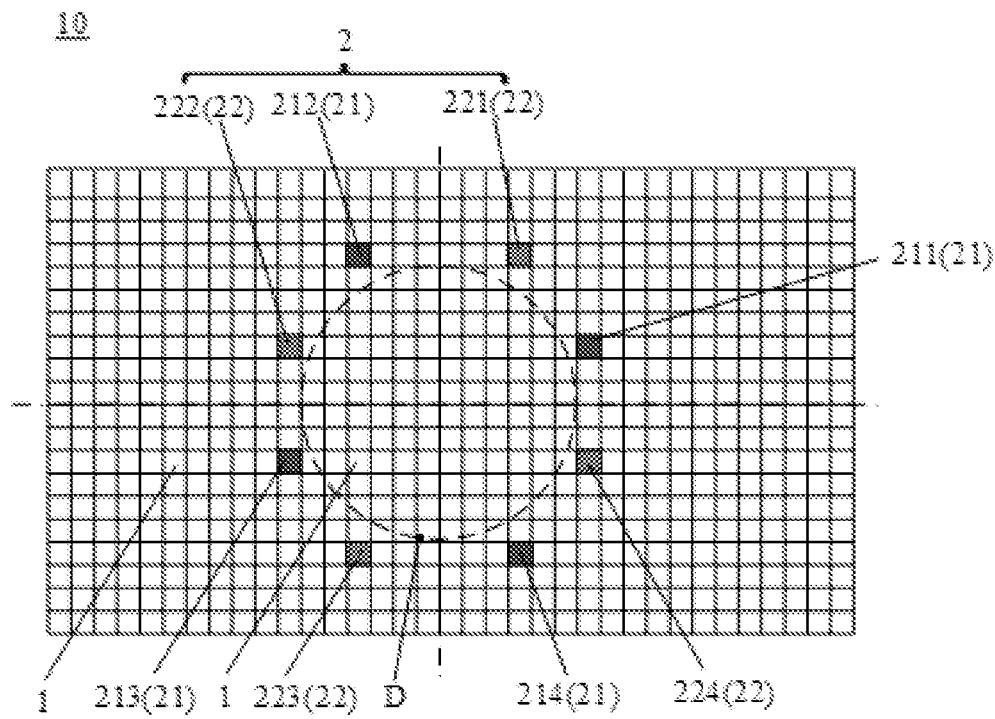
FIG. 1B is another schematic view of the flat panel detector provided by at least one embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. "In," "out," "on," "under" and the like are only used to indicate relative position relationship, and when the position of the object which is described is changed, the relative position relationship may be changed accordingly.

The drawings in the present disclosure are not drawn strictly to the actual scale, and the total number of photosensitive pixel units, first alignment pixel units, second alignment pixel units, first alignment marks and second alignment marks in a flat panel detector is not limited to the number shown in the drawings. The specific size and quantity of each element are determined according to actual needs. The drawings described in the present disclosure are only schematic structural views.

An object to be imaged is illuminated by light, and the light passing through the object to be imaged is incident onto a flat panel detector, and then the incident light incident on the flat panel detector is converted into an image electrical signal by the photosensitive element of the flat panel detector, thereby generating a charge image. During the aforementioned process, when the position of the incident light incident on the flat panel detector moves, the flat panel detector receives and responds to the incident light to generate multiple different charge images at different positions, and the positions of these charge images are located in different regions. The subsequent process needs to use the multiple real-time charge images obtained with the real-time movement of the incident light to synthesize a final image; during such process, it is necessary to use the position information of the multiple real-time charge images to synthesize the final image, thus requiring the multiple real-time charge images to be located in a preset region for synthesizing an ideal final image.

At least one embodiment of the present disclosure provides a flat panel detector, and the flat panel detector includes a plurality of pixel units arranged in an array. The plurality of pixel units include a plurality of photosensitive pixel units and a plurality of alignment pixel units. Each of the plurality of photosensitive pixel units includes a photoelectric sensor, and the photoelectric sensor is configured to convert an incident light into an electrical signal so that a photosensitive pixel unit in which the photoelectric sensor is located has a grayscale that changes according to a real-time change of the incident light. Each of the plurality of alignment pixel units is configured to have a fixed grayscale, and the fixed grayscale does not change according to the real-time change of the incident light. The plurality of alignment pixel units include a plurality of first alignment pixel units and a plurality of second alignment pixel units. Each of the plurality of first alignment pixel units has a first fixed grayscale. Each of the plurality of second alignment pixel units has a second fixed grayscale, and the first fixed grayscale is different from the second fixed grayscale. Exemplarily, FIG. 1A is a schematic view of a flat panel detector provided by at least one embodiment of the present disclosure. As illustrated in FIG. 1A, the flat panel detector 10 provided by at least one embodiment of the present disclosure includes a plurality of pixel units arranged in an array, and the plurality of pixel units include a plurality of photosensitive pixel units 1 and a plurality of alignment pixel units 2. For example, the working process of the flat panel detector 10 is as described above. Each of the plurality of photosensitive pixel units 1 includes a photoelectric sensor, and the photoelectric sensor is configured to convert an incident light into an electrical signal so that a photosensitive pixel unit in which the photoelectric sensor is located has a grayscale that changes according to a real-time change of the incident light, thereby generating a charge image. Each of the plurality of alignment pixel units is configured to have a fixed grayscale that does not change with the real-time change of the incident light, so that the plurality of alignment pixel units are identified and the position information of the plurality of alignment pixel units are obtained. The position information of the plurality of alignment pixel units is, for example, coordinates, and the coordinates of the plurality of alignment pixel units are used as a reference to determine the position of the charge image generated by the flat panel detector 10. With the real-time change of the incident light (for example, the emission source of the incident light moves relative to the object to be imaged), the position of the incident light incident on the flat panel detector 10 after passing through the object to be imaged changes, the position of the photosensitive pixel unit 1 of the flat panel detector 10 for receiving and responding to the incident light changes, and the shape and position of the formed charge image change. At this time, by calculating the distance of the charge image relative to the alignment pixel units, the position of the flat panel detector 10 is adjusted in real time so that the charge image is always located in a preset region, for example, the preset region is called as an image acquisition region. The embodiments of the present disclosure meet the above-mentioned requirement that the multiple real-time charge images generated with the change of the incident light are all located in the image acquisition region, so as to facilitate the synthesis of the ideal final image and avoid the problems of great difficulty or unsatisfactory effect encountered in synthesizing the final image due to generating different charge images in different regions. The plurality of alignment pixel units 2 include a plurality of first alignment pixel units 21 and a plurality of second alignment pixel units 22. Each of the plurality of first alignment pixel units 21 has a first fixed grayscale. Each of the plurality of second alignment pixel units 22 has a second fixed grayscale, and the first fixed grayscale is different from the second fixed grayscale. A difference exists between the grayscale of the first fixed grayscale and the grayscale of the second fixed grayscale, so that compared with only providing alignment pixel units of the same fixed grayscale, the following beneficial technical effects are obtained. During the working process of the flat panel detector 10 provided by the present disclosure, the coordinates of the plurality of first alignment pixel units 21 and the coordinates of the plurality of second alignment pixel units 22 are acquired simultaneously, so that in the case where the grayscales of the photosensitive pixel units 1 change, for example, in the case where the grayscales of most or all of the photosensitive pixel units 1 are close to the grayscale of the first alignment pixel units 21, the second alignment pixel units 22 are accurately identified; or, in the case where the grayscales of most or all of the photosensitive pixel units 1 are close to the grayscale of the second alignment pixel units 22, the first alignment pixel units 21 are accurately identified. Under any circumstances, the alignment pixel units are accurately identified, so as to achieve more accurate alignment.

For example, the incident light mentioned above is X-ray. For example, during the imaging process, the emission source of the X-ray moves or the object to be imaged moves, for example, the X-ray rotates around the object to be imaged. When the emission source of the X-ray rotates at different angles, the flat panel detector 10 is used to form the multiple real-time charge images of the object to be imaged at multiple different angles, and to convert the multiple charge images into digital images. The multiple charge images are located in the image acquisition region that is preset to facilitate the use of the position information of each charge image, so that the generated digital image is always located in a display region that is preset, which is beneficial to the imaging effect and convenience of operation, and improves the work efficiency of using the flat panel detector 10 to obtain the required images. For example, a real-time stereoscopic three-dimensional image is obtained by synthesizing multiple digital images.

For example, the flat panel detector 10 is used in the field of medical detection, using X-ray to form an image of a part (such as an organ) of the human body. In this case, by allowing a plurality of real-time charge images to be located in the image acquisition region, the flat panel detector 10 provided by the embodiments of the present disclosure forms the image of the object to be detected, such as the organ to be detected, with an ideal effect (for example, an ideal three-dimensional image), which more truly and accurately reflects the morphology of the object to be detected, obtains more real and accurate image information, improves the accuracy of the detection result, and improves the imaging speed. For example, the incident light mentioned above is visible light, and a color plane image or a color three-dimensional image is formed. The application scenarios and imaging types of the flat panel detector provided by the embodiments of the present disclosure are not limited to the above situations.

For example, in the embodiment illustrated in FIG. 1A, the plurality of first alignment pixel units 21 are respectively the first alignment pixel units 211, 212, 213, and 214, and the plurality of second alignment pixel units 22 are respectively the second alignment pixel units 221, 222, 223, and 224.

For example, in the embodiment illustrated in FIG. 1A, the plurality of first alignment pixel units 211, 212, 213, and 214 and the plurality of second alignment pixel units 221, 222, 223, and 224 surround the image acquisition region D that is preset. In this way, positioning can be performed around the entire image acquisition region D, which is more conducive to accurate positioning. The shape of the image acquisition region D is not limited to that illustrated in FIG. 1A. For example, the shape of the image acquisition region D is a rectangle, that is, a region surrounded by the plurality of first alignment pixel units and the plurality of second alignment pixel units is a rectangular region.

Figure 1B:
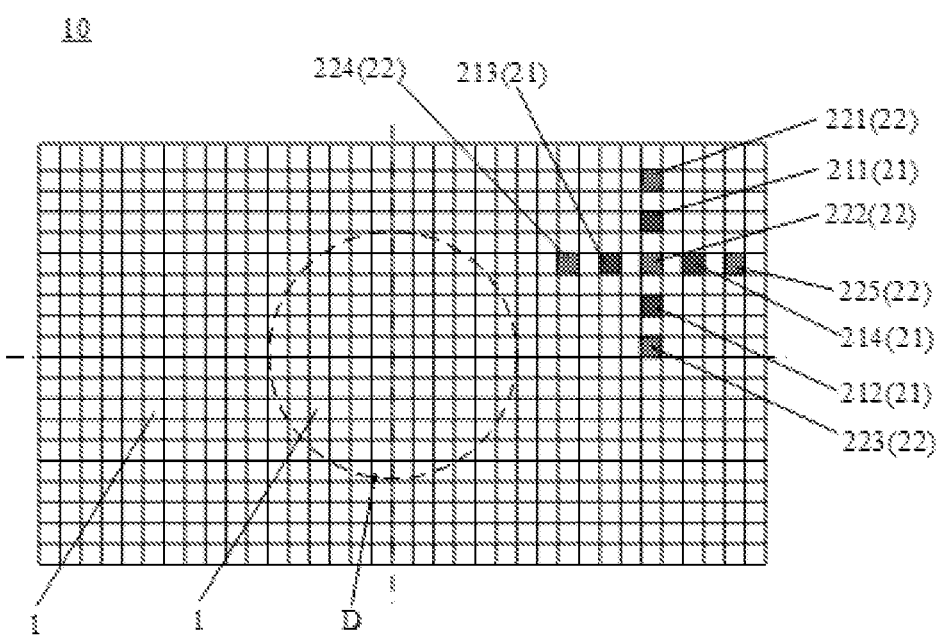
Figure 2:
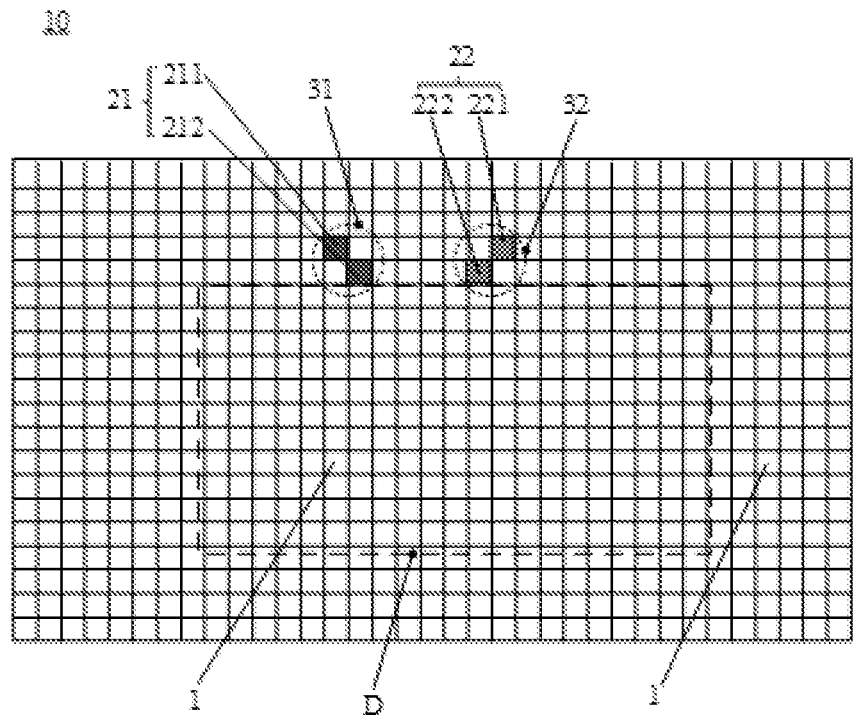
FIG. 2 is another schematic view of the flat panel detector provided by at least one embodiment of the present disclosure.

Of course, the embodiments of the present disclosure are not limited to the situation where the plurality of alignment pixel units surround the image acquisition region D. For example, FIG. 1B is another schematic view of the flat panel detector provided by an embodiment of the present disclosure. In the embodiment illustrated in FIG. 1B, the plurality of first alignment pixel units 211, 212, 213, and 214 and the plurality of second alignment pixel units 221, 222, 223, 224, and 225 are arranged in a cross shape, and the plurality of first alignment pixel units 21 and the plurality of second alignment pixel units 22 are located on one side of the image acquisition region D. For example, FIG. 2 is another schematic view of the flat panel detector provided by an embodiment of the present disclosure. In FIG. 2, the first alignment pixel units 211 and 212 and the second alignment pixel units 221 and 222 are located on one side of the image acquisition region D. In other embodiments, the plurality of first alignment pixel units and the plurality of second alignment pixel units for example are arranged in other shapes, for example, in a line shape or a shape of ✹, which is not limited in the embodiments of the present disclosure.

For example, the first alignment pixel units 211, 212, 213, 214 are alternately arranged with the second alignment pixel units 221, 222, 223, 224, that is, along the arrangement direction of the first alignment pixel units and the second alignment pixel units, the second alignment pixel unit 221 and the second alignment pixel unit 222 are respectively located on two sides of the first alignment pixel unit 212 and adjacent to the first alignment pixel unit 212, the first alignment pixel unit 211 is located on a side of the second alignment pixel unit 221 away from the first alignment pixel unit 212 and is adjacent to the second alignment pixel unit 221, and the first alignment pixel unit 213 is located on a side of the second alignment pixel unit 222 away from the first alignment pixel unit 212 and is adjacent to the second alignment pixel unit 222. The alternating arrangement of the first alignment pixel units and the second alignment pixel units allows the grayscale difference of the adjacent alignment pixel units more obvious, which is beneficial to improve the accuracy of identifying the first alignment pixel units and the second alignment pixel units, thereby improving the accuracy and reliability of positioning.

For example, the absolute value of the difference between the first fixed grayscale and the second fixed grayscale is greater than or equal to 30% of the absolute value of the difference between the maximum grayscale and the minimum grayscale of the plurality of photosensitive pixel units, so that an obvious grayscale difference is between each of the first alignment pixel units 211, 212, 213, and 214 and each of the alignment second pixel units 221, 222, 223, and 224. In the case where the grayscales of most or all of the photosensitive pixel units 1 are each close to the grayscale of one of the first alignment pixel unit and the second alignment pixel unit, the recognition degree of the other of the first alignment pixel unit and the second alignment pixel unit is improved, so that accurate positioning is also achieved. For example, there are $2^{16}$ grayscales in total, and the difference between the first fixed grayscale and the second fixed grayscale is greater than 20,000 grayscales.

For example, each of the plurality of first alignment pixel units 21 is a normally black pixel unit, and each of the plurality of second alignment pixel units 22 is a normally white pixel unit. The normally black pixel unit is always in a black state, and the normally white pixel unit is always in a bright state, for example, the brightness of the bright state is always the highest achievable brightness. In this way, when the flat panel detector 10 is in a black state as a whole, the first alignment pixel unit 21 that is always in the bright state is accurately identified; and when the flat panel detector 10 is in a bright state as a whole, the second alignment pixel unit 22 that is always in the dark state is accurately identified. That is, when the flat panel detector 10 as a whole is in the black state or the bright state, the effect of accurate positioning is guaranteed.

For example, at least two of the plurality of first alignment pixel units form a first alignment mark, and at least two of the plurality of second alignment pixel units form a second alignment mark, so as to increase the area of the first alignment mark and the second alignment mark that can be identified, thereby improving the reliability and accuracy of positioning.

Figure 3:
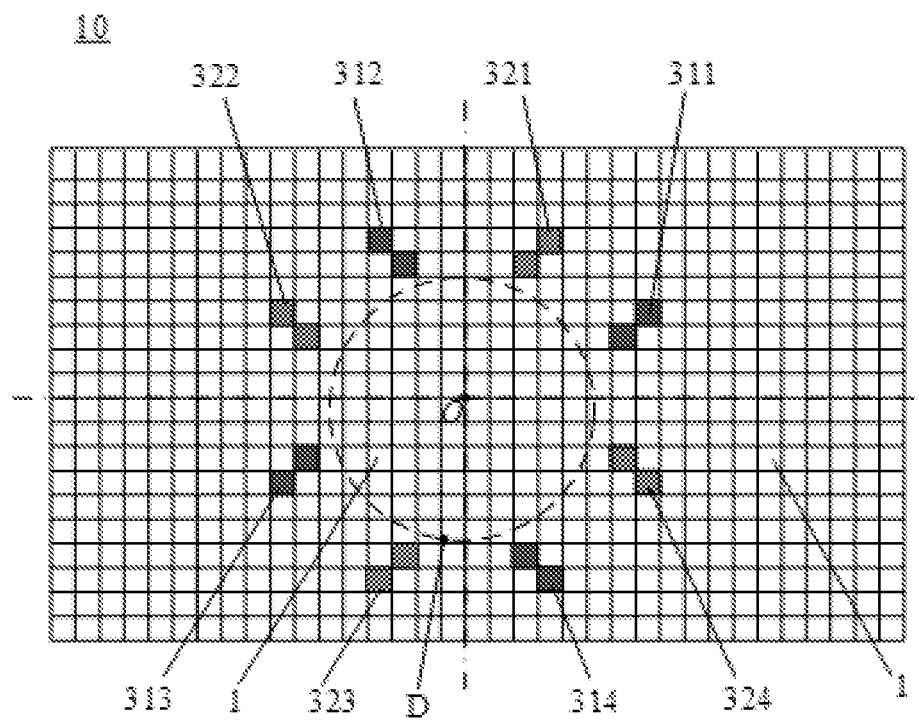
FIG. 3 is yet another schematic view of the flat panel detector provided by at least one embodiment of the present disclosure.

Exemplarily, in the embodiments illustrated in FIG. 2 and FIG. 3, two of the plurality of first alignment pixel units 21 form a first alignment mark 31, and the two first alignment pixel units 211 and 212 located in the same first alignment mark 31 are respectively located in adjacent columns and adjacent rows of the plurality of pixel units arranged in an array. Two of the plurality of second alignment pixel units 22 form a second alignment mark 32, and the two second alignment pixel units 221 and 222 located in the same second alignment mark 32 are respectively located in adjacent columns and adjacent rows of the plurality of pixel units arranged in an array. That is, two diagonally adjacent first alignment pixel units form the first alignment mark 31, and two diagonally adjacent second alignment pixel units form the second alignment mark 32. It has been verified by experiments that such a design is beneficial to improve the accuracy of identifying the first alignment mark 31 and the second alignment mark 32. The alignment mark formed by the combination of the alignment pixel units is beneficial to improve the accuracy of identification, avoid misidentification caused by the confusion between simple mark of single alignment pixel unit and dead pixel unit. Furthermore, the alignment mark formed by the combination of pixel units has a simple design.

For example, as illustrated in FIG. 3, the first alignment marks 311, 312, 313, and 314 are alternately arranged with the second alignment marks 321, 322, 323, and 324. That is, along the arrangement direction of the first alignment marks and the second alignment marks, the second alignment mark 321 and the second alignment mark 322 are respectively located on two sides of the first alignment mark 312 and are respectively adjacent to the first alignment mark 312, the first alignment mark 311 is located on the side of the second alignment mark 321 away from the first alignment mark 312 and adjacent to the second alignment mark 321, and the first alignment mark 313 is located on the side of the second alignment mark 322 away from the first alignment mark 312 and adjacent to the second alignment mark 322. The alternating arrangement of the first alignment marks and the second alignment marks allows the grayscale difference of the adjacent alignment marks more obvious, which is beneficial to improve the accuracy of identifying the first alignment marks and the second alignment marks, thereby improving the accuracy and reliability of positioning.

For example, as illustrated in FIG. 3, the plane pattern formed by the arrangement of the plurality of first alignment marks 311, 312, 313, and 314 and the plurality of second alignment marks 321, 322, 323, and 324 is a centrosymmetric pattern. For example, the plane pattern is centrosymmetric with the point 0 in FIG. 3 as the symmetry center. For example, each pair of the first alignment marks is centrosymmetric with the point O as the symmetry center, and each pair of the second alignment marks is centrosymmetric with the point O as the symmetry center. The first alignment mark 311 and the first alignment mark 313 are centrosymmetric, the first alignment mark 312 and the first alignment mark 314 are centro symmetric, the second alignment mark 321 and the second alignment mark 323 are centrosymmetric, and the second alignment mark 322 and the second alignment mark 324 are centrosymmetric.

Other unmentioned features and effects of the embodiment illustrated in FIG. 3 are the same as those of the embodiment illustrated in FIG. 1A.

Figure 4:
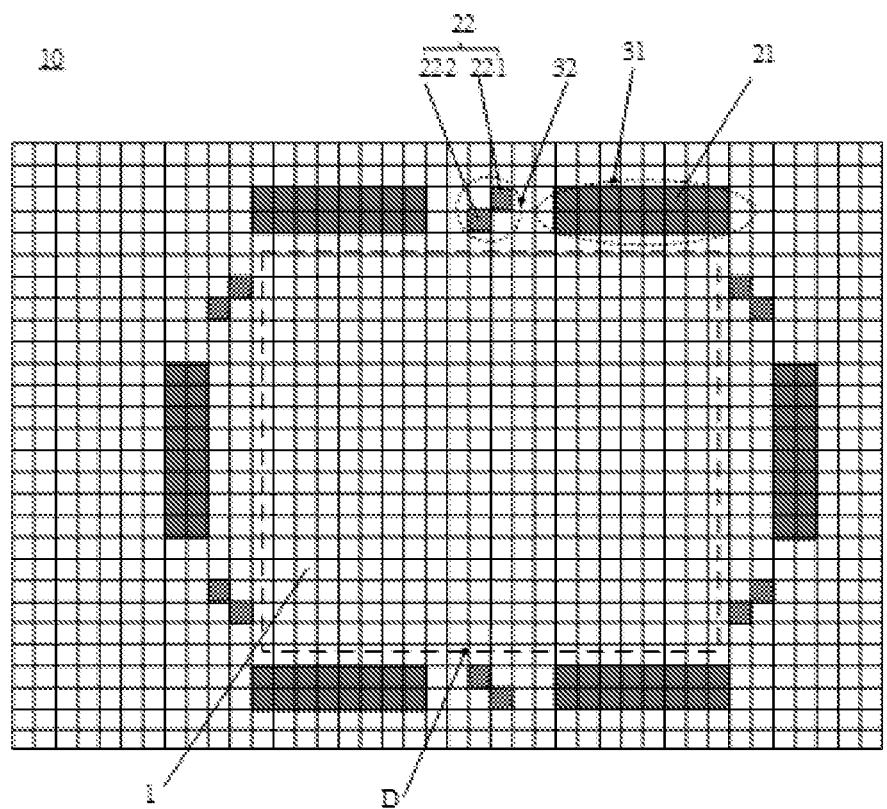
FIG. 4 is still another schematic view of the flat panel detector provided by at least one embodiment of the present disclosure.

FIG. 4 is still another schematic view of the flat panel detector according to an embodiment of the present disclosure, and this embodiment has the following differences from the embodiment illustrated in FIG. 3. As illustrated in FIG. 4, the total number of the first alignment pixel units 21 included in each first alignment mark 31 is greater than the total number of the second alignment pixel units 22 included in each second alignment mark 32. In this way, the area of the first alignment mark is increased, and the accuracy of identifying a darker first alignment mark is higher.

For example, m*n first alignment pixel units of the plurality of first alignment pixel units form the first alignment mark, and m and n are both positive integers. In this way, in the case where the flat panel detector 10 adopts synchronous multi-row scanning, m rows of pixel units are scanned at the same time, so that the first alignment pixel units located in m rows and constituting the first alignment mark are simultaneously identified. Then, while the accuracy of identifying the first alignment mark is improved, the identification operation and the design of the circuit for identifying the first alignment mark are facilitated.

For example, as illustrated in FIG. 4, 2*8 first alignment pixel units 21 of the plurality of first alignment pixel units form the first alignment mark 31, and the same is true for each first alignment mark, that is, in each first alignment mark, m=2, n=8. For example, two second alignment pixel units of the plurality of second alignment pixel units form the second alignment mark 32, and the two second alignment pixel units 221 and 222 located in the same second alignment mark are respectively located in adjacent columns and adjacent rows of the plurality of pixel units arranged in an array.

For example, in FIG. 4, the plane pattern formed by the arrangement of the plurality of first alignment marks and the plurality of second alignment marks is not a centrosymmetric pattern. For example, the plane pattern formed by the arrangement of the plurality of first alignment marks and the plurality of second alignment marks is an axisymmetric pattern. The regular arrangement is beneficial to the convenience and accuracy of identification. However, the embodiments of the present disclosure do not limit the plane pattern formed by the arrangement of the plurality of first alignment marks and the plurality of second alignment marks.

For example, in FIG. 4, the image acquisition region D for acquiring image information includes at least part of the plurality of photosensitive pixel units 1. For example, the flat panel detector 10 further includes the photosensitive pixel units 1 located outside the image acquisition region D. For example, the plurality of first alignment marks 31 and the plurality of second alignment marks 32 surround the image acquisition region D to perform positioning around the entire image acquisition region D, which is more conducive to accurate positioning.

For example, the plurality of first alignment marks 31 and the plurality of second alignment marks 32 are evenly distributed in the circumferential direction of the image acquisition region D, so that the positions of the final charge image in any direction of the image acquisition region D are all located in the image acquisition region D more accurately.

Of course, in other embodiments, the plurality of first alignment marks 31 and the plurality of second alignment marks 32 may not surround the image acquisition region D.

Other unmentioned features and effects of the embodiment illustrated in FIG. 4 are the same as those of the embodiment illustrated in FIG. 3.

Figure 5A:
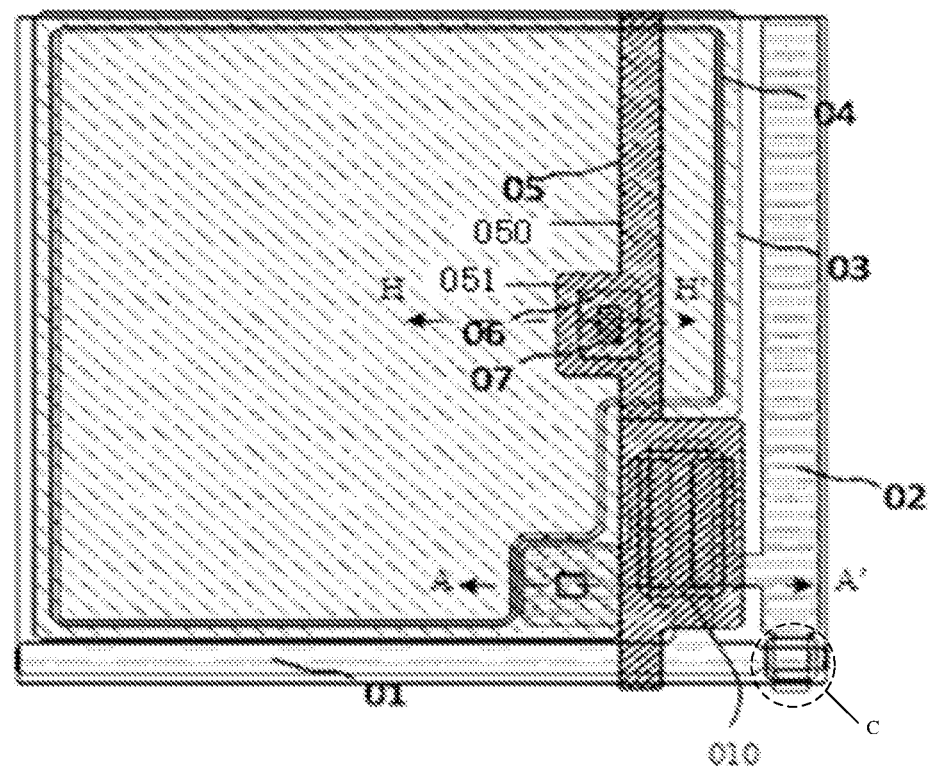
FIG. 5A is a plan view of a photosensitive pixel unit of the flat panel detector provided by at least one embodiment of the present disclosure.
Figure 5B:
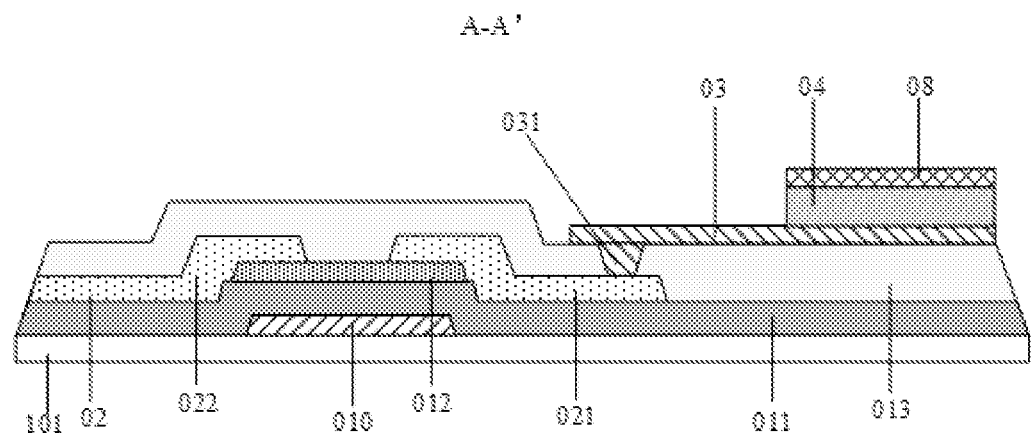
FIG. 5B is a schematic cross-sectional view along line A-A' in FIG. 5A.
Figure 5C:
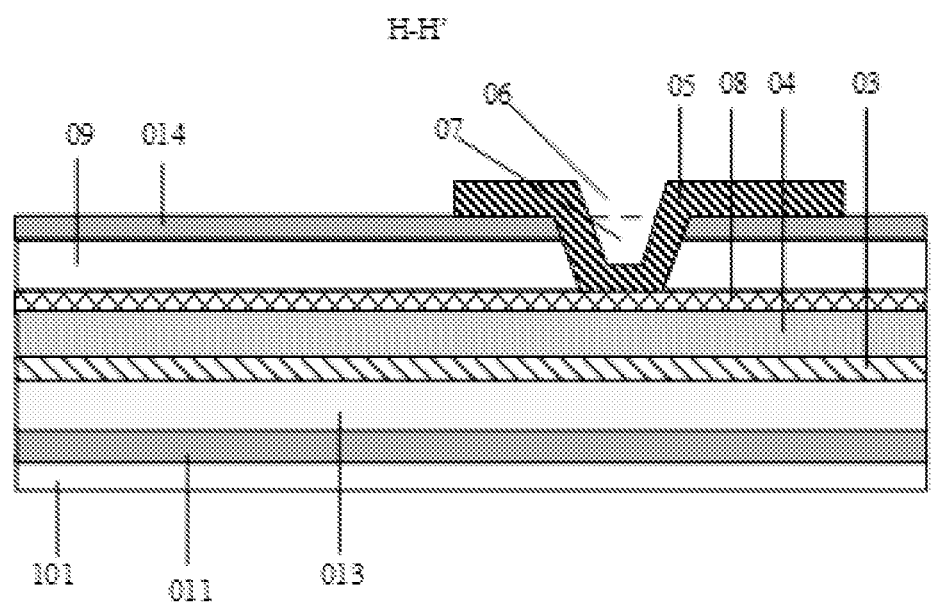
FIG. 5C is a schematic cross-sectional view along line H-H' in FIG. 5A.

FIG. 5A is a plan view of the photosensitive pixel unit of the flat panel detector provided by an embodiment of the present disclosure, FIG. 5B is a schematic cross-sectional view along line A-A' in FIG. 5A, and FIG. 5C is a schematic cross-sectional view along line H-H' in FIG. 5A. Referring to FIG. 5A-FIG. 5C, the photoelectric sensor includes a first electrode 03, a photoelectric sensing layer 04 and a second electrode 08. The photoelectric sensing layer 04 is stacked with the first electrode 03 and is configured to convert the incident light into an electrical signal, and the electrical signal is configured to control the real-time grayscale of the corresponding photosensitive pixel unit 1. The second electrode is located on the side of the photoelectric sensing layer 04 away from the first electrode. Each of the plurality of photosensitive pixel units 1 includes a transistor including a gate electrode 010, a first electrode 021 and a second electrode 022. The flat panel detector 10 further includes signal lines including a bias voltage line 05, a gate line 01 and a data line 02. The bias voltage line 05 is electrically connected with the second electrode 08 of the photoelectric sensor and is configured to provide a bias voltage to the photosensitive pixel unit 1. The gate line 01 is electrically connected with the gate electrode 010, and is configured to provide a gate driving signal to the transistor. The data line 02 intersects the gate line 010 to define a plurality of pixel units arranged in an array. In each photosensitive pixel unit 1, the first electrode 021 of the transistor is electrically connected with the first electrode 03 of the photoelectric sensor, and the data line 02 is electrically connected with the second electrode 022 of the transistor to read the electrical signal generated by the photoelectric sensing layer 04.

For example, the transistor mentioned above is a thin film transistor. The thin film transistor for example is an amorphous silicon thin film transistor, an oxide thin film transistor, or a low temperature polysilicon (LTPS) thin film transistor. The thin film transistor for example has a top-gate structure or a bottom-gate structure. The embodiments of the present disclosure do not limit the type of the thin film transistor, which can be selected according to specific needs.

For example, the photoelectric sensor is a photodiode, including a PIN junction. For example, the photoelectric sensing layer 04 includes an N-type semiconductor layer, an intrinsic semiconductor layer, and a P-type semiconductor layer. The first electrode of the thin film transistor is electrically connected with the N-type semiconductor layer. In the case where the incident light is X-ray, the flat panel detector 10 is provided with a scintillator layer, and the scintillator layer converts the X-ray into visible light, and the visible light illuminates the photosensitive pixel unit. The working process of the flat panel detector 10 is as follows: X-ray is modulated by the human body, the X-ray that is modulated is converted into visible light by the scintillator layer, the visible light is absorbed by the photodiode and converted into charge carriers, and the charge carriers are stored in the self-capacitance of the photodiode or in the storage capacitor separately provided to form a charge image by the flat panel detector 10. A scanning drive circuit sequentially turns on the thin film transistors of the photosensitive pixel units in each row, and outputs the charge image in the manner of reading out one row at the same time, that is, outputs the electrical signal generated by each photosensitive pixel unit. The charge image read out by each thin film transistor corresponds to the dose of incident X-ray, and the charge amount of each photosensitive region is determined through processing, and then the dose of the X-ray of each photosensitive region is determined. A black-and-white image or a color image is generated by a display device using the electrical signal generated by the photosensitive pixel unit.

For example, the bias voltage mentioned above is a common voltage, such as a ground voltage or other types of common voltages. The bias voltage line 05 is connected with each photosensitive pixel unit 1.

For example, as illustrated in FIG. 5B, the flat panel detector 10 further includes a gate insulating layer 011 and an interlayer insulating layer 013 which is between the thin film transistor and the first electrode 03 of the photoelectric sensor. The first electrode 021 of the transistor is electrically connected with the first electrode 03 of the photoelectric sensor through a first via hole 031 penetrating the interlayer insulating layer 013.

For example, as illustrated in FIG. 5C, the flat panel detector 10 further includes a first insulating layer 09 located on a side of the photoelectric sensor away from a base substrate 101 and a second insulating layer 014 located on a side of the first insulating layer 09 away from the base substrate 101. For example, the first insulating layer 09 is an organic insulating layer. For example, the first insulating layer 09 is a planarization layer. For example, the first insulating layer 09 is made of an organic material, such as resin, or a photoresist material. For example, the second insulating layer 014 is an inorganic insulating layer and is made of an inorganic material, for example, the inorganic material includes at least one of silicon oxide, silicon nitride and silicon oxynitride. For example, the bias voltage line 05 is electrically connected with the second electrode 08 of the photoelectric sensor through a second via hole 06 penetrating the second insulating layer 014 and a third via hole 07 penetrating the first insulating layer 09. For example, the second via hole 06 and the third via hole 07 are communicated with each other. For example, the flat panel detector 10 further includes a third insulating layer (not illustrated) on a side of the first insulating layer 09 close to the second electrode 08. The third insulating layer is an inorganic insulating layer, and its material includes at least one of silicon oxide, silicon nitride and silicon oxynitride.

For example, the base substrate 101 is a rigid substrate, and the material of the rigid substrate includes one of glass, quartz, and metal. For example, the base substrate 101 is a flexible substrate, and the material of the flexible substrate includes one of polyimide (PI for short), polyethylene terephthalate (PET for short), polyethylenenaphthalate two formic acid glycol ester (PEN for short), polycarbonate (PC for short), and other polymers.

As illustrated in FIG. 5A, for example, the bias voltage line 05 includes a main body portion 050 and a protrusion portion 051. The protrusion portion 051 is connected with the main body portion 050 and protrudes from the main body portion 050, and the orthographic projections of the second via hole 06 and the third via hole 07 on the base substrate 101 are located within the orthographic projection of the protrusion portion 051 on the base substrate 101. The protrusion portion 051 for example is formed by a patterning process, and the second via hole 06 and the third via hole 07 provide sufficient space, which can reduce the difficulty of patterning, thereby accurately forming the second via hole 06 and the third via hole 07. For example, the gate line 01 extends in a first direction, the data line 02 extends in a second direction, for example, the bias voltage line 05 extends in the second direction, and the protrusion portion 051 protrudes from the main body portion 050 in the first direction.

As illustrated in FIG. 5A, the gate line 01 overlaps with the data line 02 as illustrated in a region C in FIG. 5A, that is, the orthographic projection of the gate line 01 on the base substrate 101 overlaps with the orthographic projection of the data line 02 on the base substrate 101; and in the region C where the orthographic projection of the gate line 01 on the base substrate 101 overlaps with the orthographic projection of the data line 02 on the base substrate 101, the line widths of the gate line 01 and the data line 02 both decrease. That is, the line width of a part of the gate line 01 that overlaps with the data line 02 is smaller than the line width of a part of the gate line 01 that does not overlap with the data line 02, and the line width of a part of the data line 02 that overlaps with the gate line 01 is smaller than the line width of a part of the data line 02 that does not overlap with the gate line 01. In addition, an isolation layer is provided in the region C, the isolation layer and an active layer of the transistor are provided in the same layer, and the isolation layer is located between the gate line 01 and the data line 02, which can further prevent signal crosstalk between the gate line 01 and the data line 02.

For example, each of the plurality of first alignment pixel units also includes the transistor and the photoelectric sensor. In at least part (at least some of the plurality of alignment pixel units) of the first alignment pixel units, the transistors and the signal lines form an open circuit, so that the data lines are incapable of reading the electrical signals generated by the photoelectric sensing layers, so as to realize that the at least part of the first alignment pixel units are normally black pixel units.

Figure 6A:
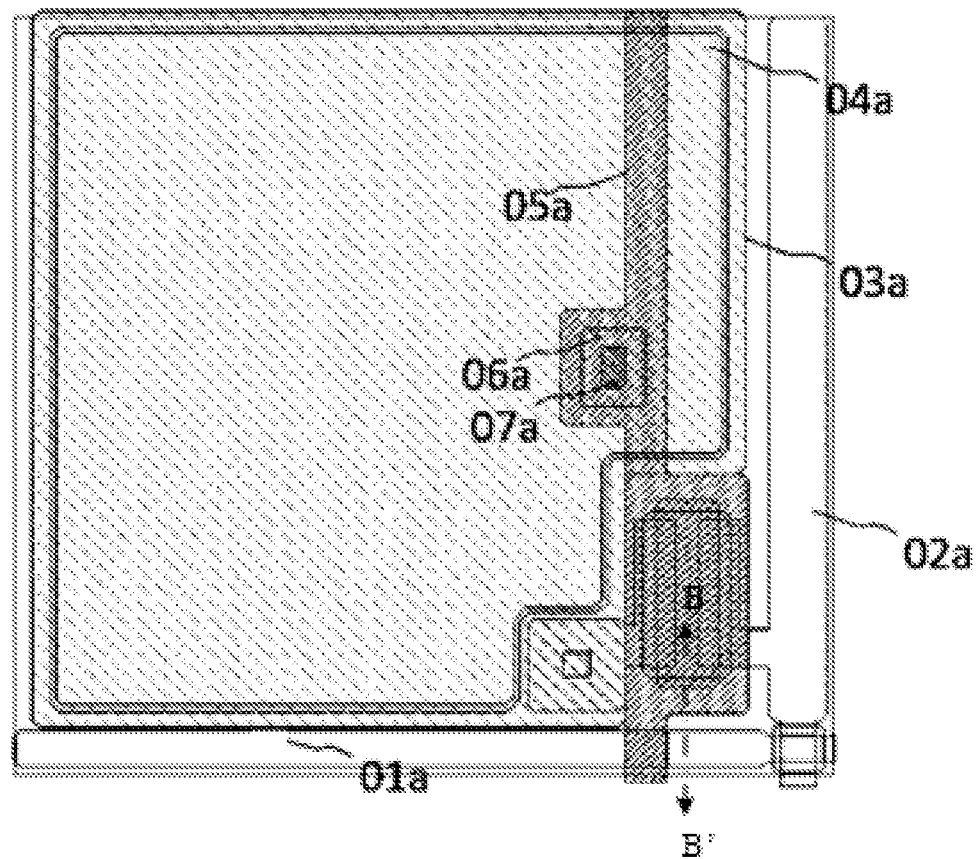
FIG. 6A is a plan view of a first alignment pixel unit of the flat panel detector provided by at least one embodiment of the present disclosure.
Figure 6B:
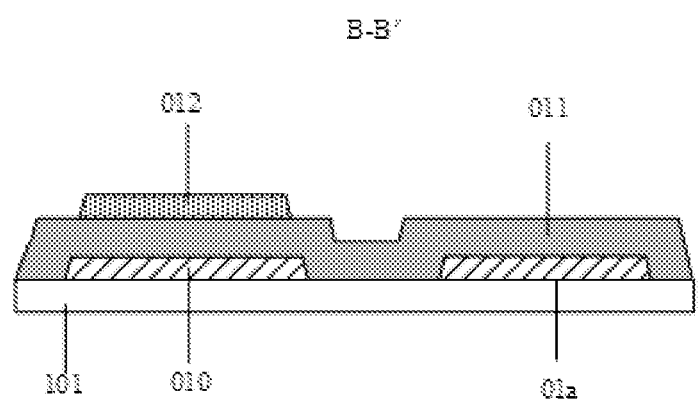
FIG. 6B is a schematic cross-sectional view along line B-B' in FIG. 6A.

Exemplarily, FIG. 6A is a plan view of the first alignment pixel unit of the flat panel detector provided by an embodiment of the present disclosure, and FIG. 6B is a schematic cross-sectional view along the line B-B' in FIG. 6A. Referring to FIG. 6A-FIG. 6B, each first alignment pixel unit includes the transistor and the photoelectric sensor. The difference between the structure of the first alignment pixel unit illustrated in FIG. 6A-FIG. 6B and the structure of the photosensitive pixel unit 1 illustrated in FIG. 5A-FIG. 5C is that the gate electrode 010 of the transistor of the first alignment pixel unit is disconnected from the gate line 01a, that is, the gate electrode 010 of the transistor of the first alignment pixel unit is not connected with the gate line 01a, so that the thin film transistor cannot be turned on, and the data line 02a is incapable of reading the electrical signal generated by the photoelectric sensing layer. The first alignment pixel unit is a normally black pixel unit. Other features of the gate line 01a here are the same as the gate line 01 illustrated in FIG. 5A-FIG. 5C, and the data line 02a is the same as the data line 02 illustrated in FIG. 5A-FIG. 5C. For example, other unmentioned structures of the first alignment pixel unit, such as the semiconductor layer 012, the first electrode and the second electrode of the thin film transistor, the first electrode 03a, the photoelectric sensing layer 04a and the second electrode 05a of the photoelectric sensor, the second via hole 06a, the third via hole 07a, and the like are all the same as those of the photosensitive pixel unit 1.

Figure 7A:
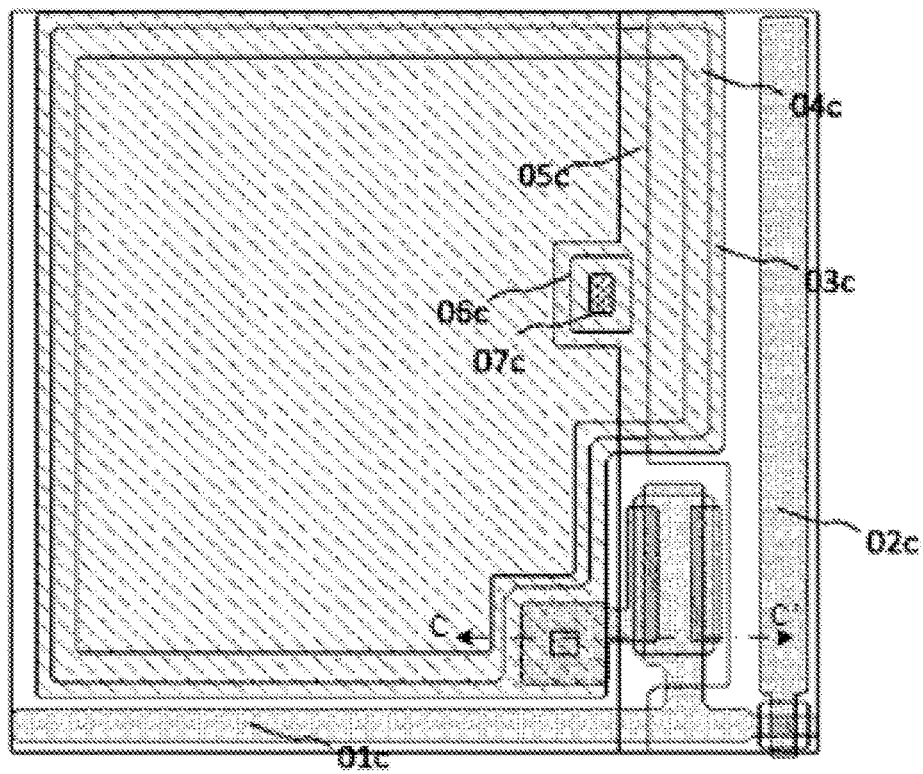
FIG. 7A is another plan view of the first alignment pixel unit of the flat panel detector provided by at least one embodiment of the present disclosure.
Figure 7B:
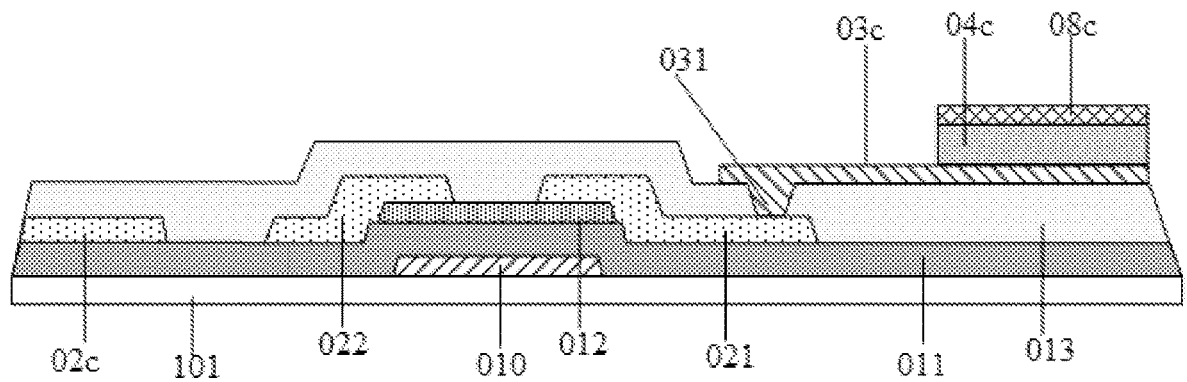
FIG. 7B is a schematic cross-sectional view along line C-C' in FIG. 7A.

For another example, FIG. 7A is another plan view of the first alignment pixel unit of the flat panel detector provided by an embodiment of the present disclosure, and FIG. 7B is a schematic cross-sectional view along the line C-C' in FIG. 7A. In the first alignment pixel unit illustrated in FIG. 7A-FIG. 7B, the second electrode 022 of the transistor is disconnected from the data line 02c, that is, the second electrode 022 of the transistor is not connected with the data line 02c, so that the thin film transistor and the signal line 02c form an open circuit and the data line 02c is incapable of reading the electrical signal generated by the photoelectric sensing layer, and the first alignment pixel unit is a normally black pixel unit. The gate line 01a illustrated in FIG. 7A-FIG. 7B is the same as the gate line 01 illustrated in FIG. 5A-FIG. 5C, and other features of the data line 02c are the same as the data line 02 illustrated in FIG. 5A-FIG. 5C. For example, other unmentioned structures of the first alignment pixel unit, such as the semiconductor layer 012, the first electrode 021 and the second electrode 022 of the thin film transistor, the first electrode 03c, the photoelectric sensing layer 04c and the second electrode 05c of the photoelectric sensor, and the like are all the same as those of the photosensitive pixel unit 1.

Figure 8A:
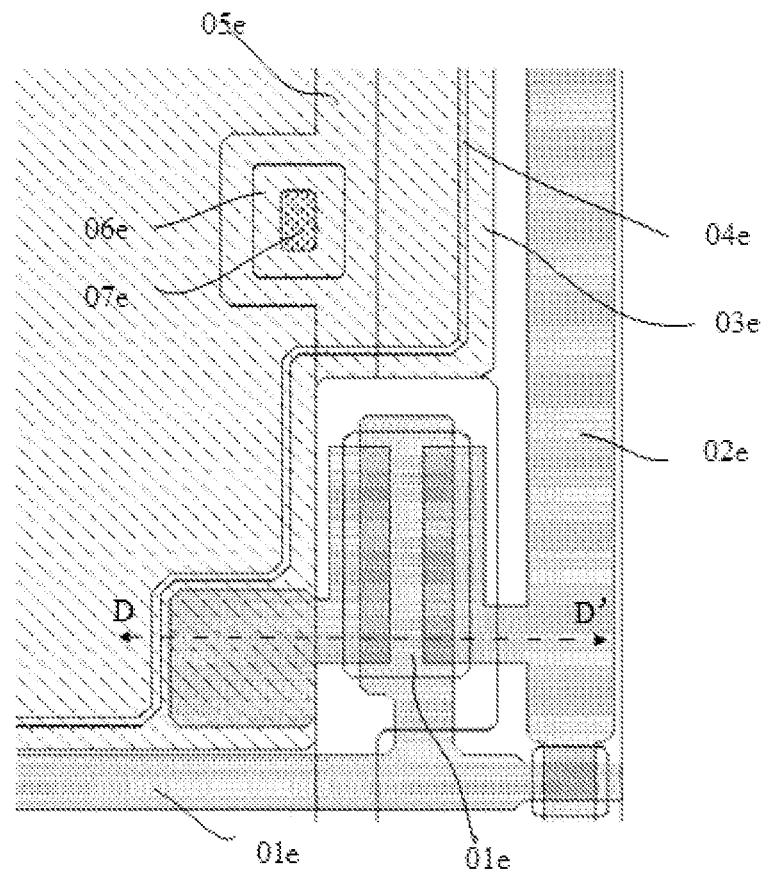
FIG. 8A is yet another plan view of the first alignment pixel unit of the flat panel detector provided by at least one embodiment of the present disclosure.
Figure 8B:
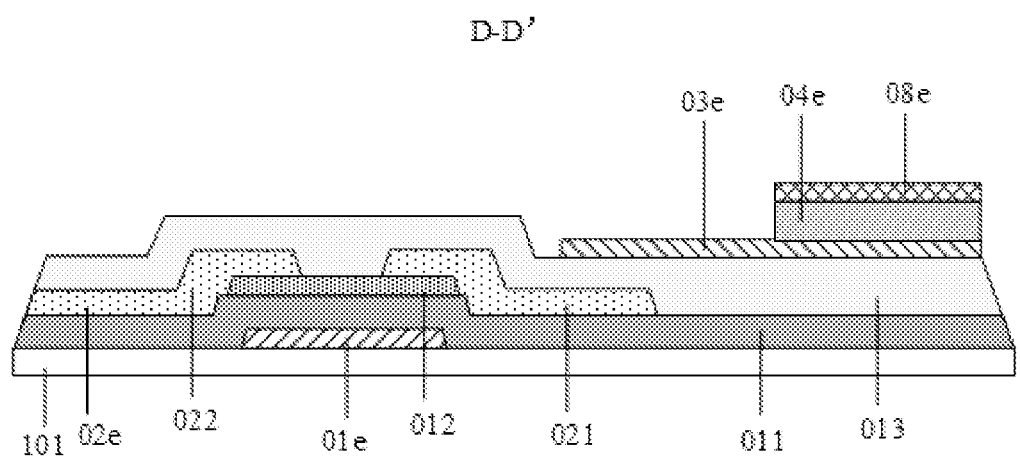
FIG. 8B is a schematic cross-sectional view along line D-D' in FIG. 8A.

For another example, FIG. 8A is another plan view of the first alignment pixel unit of the flat panel detector provided by an embodiment of the present disclosure, and FIG. 8B is a schematic cross-sectional view along the line D-D' in FIG. 8A. In the first alignment pixel unit illustrated in FIG. 8A-FIG. 8B, the first electrode 021 of the transistor is disconnected from the first electrode 03e of the photoelectric sensor of the first alignment pixel unit, that is, the first electrode 021 of the transistor is not connected with the first electrode 03e of the photoelectric sensor of the first alignment pixel unit, so that the thin film transistor and the first electrode 03e of the photoelectric sensor form an open circuit and the data line 02e is incapable of reading the electrical signal generated by the photoelectric sensing layer, and the first alignment pixel unit is a normally black pixel unit. The data line 02e here is the same as the data line 02 illustrated in FIG. 5A-FIG. 5C. As illustrated in FIG. 8B, the first electrode 03e of the photoelectric sensor and the first electrode 021 are provided in different layers, and the first electrode 03e of the photoelectric sensor and the first electrode 021 are not connected by a via hole. For example, other unmentioned structures of the first alignment pixel unit, such as the semiconductor layer 012, the first electrode 021 and the second electrode 022 of the thin film transistor, the first electrode 03e, the photoelectric sensing layer 04e and the second electrode 05e of the photoelectric sensor, and the like are all the same as those of the photosensitive pixel unit 1.

Figure 8C:
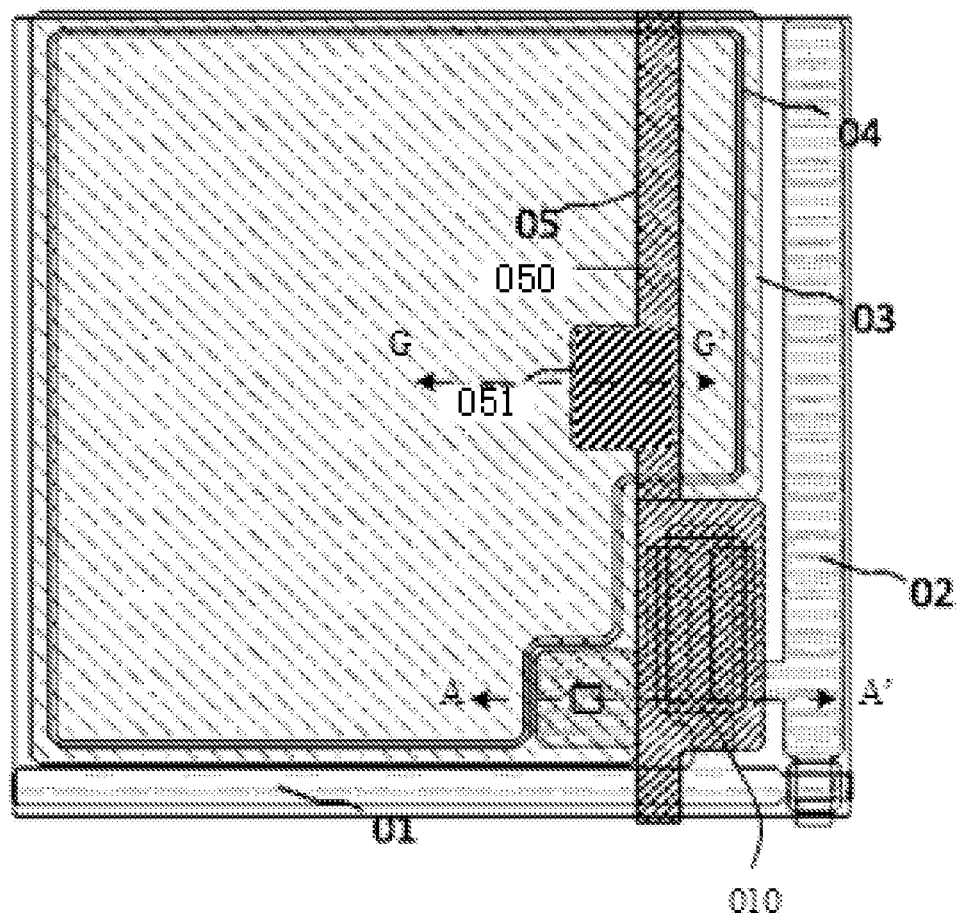
FIG. 8C is yet another plan view of the first alignment pixel unit of the flat panel detector provided by at least one embodiment of the present disclosure.
Figure 8D:
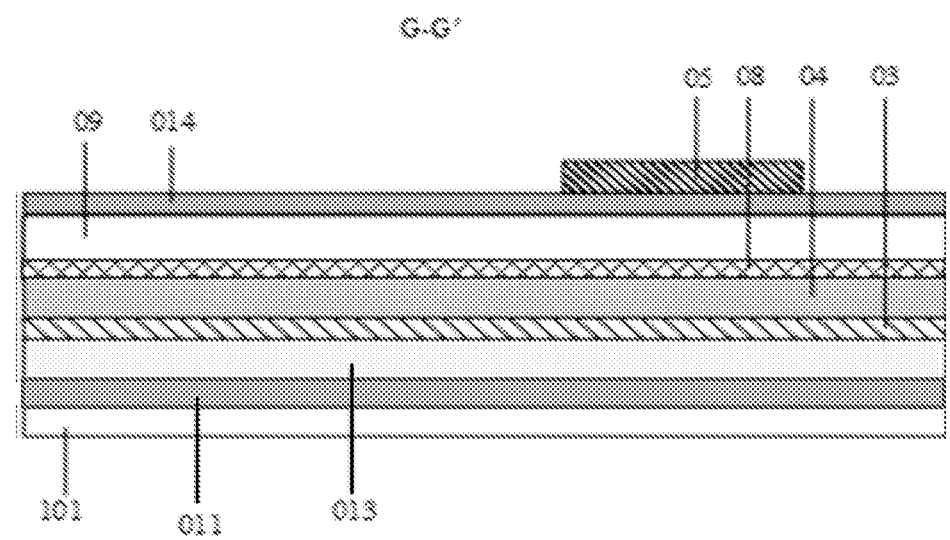
FIG. 8D is a schematic cross-sectional view along line G-G' in FIG. 8C.

FIG. 8C is still another plan view of the first alignment pixel unit of the flat panel detector provided by an embodiment of the disclosure, and FIG. 8D is a schematic cross-sectional view along the line G-G' in FIG. 8C. In the first alignment pixel unit illustrated in FIG. 8C-FIG. 8D, the bias voltage line 05 is disconnected from the photoelectric sensor of the first alignment pixel unit. As illustrated in FIG. 8D, for example, the first insulating layer 09 and the second insulating layer 014 are provided between the bias voltage line 05 and the second electrode 08 of the photoelectric sensor of the first alignment pixel unit, so that the bias voltage line 05 is insulated from the second electrode 08 of the photoelectric sensor of the first alignment pixel unit, so that the bias voltage line 05 is disconnected from the photoelectric sensor of the first alignment pixel unit. That is, the bias voltage line 05 is not electrically connected with the photoelectric sensor of the first alignment pixel unit, so that the thin film transistor and the photoelectric sensor cannot transmit electrons, and the data line 02e cannot read the electrical signal generated by the photoelectric sensing layer. The first alignment pixel unit is a normally black pixel unit. For example, other features except that the bias voltage line 05 is discon- nected from the photoelectric sensor of the first alignment pixel unit are the same as those in FIG. 5A-FIG.5C.

Figure 9A:
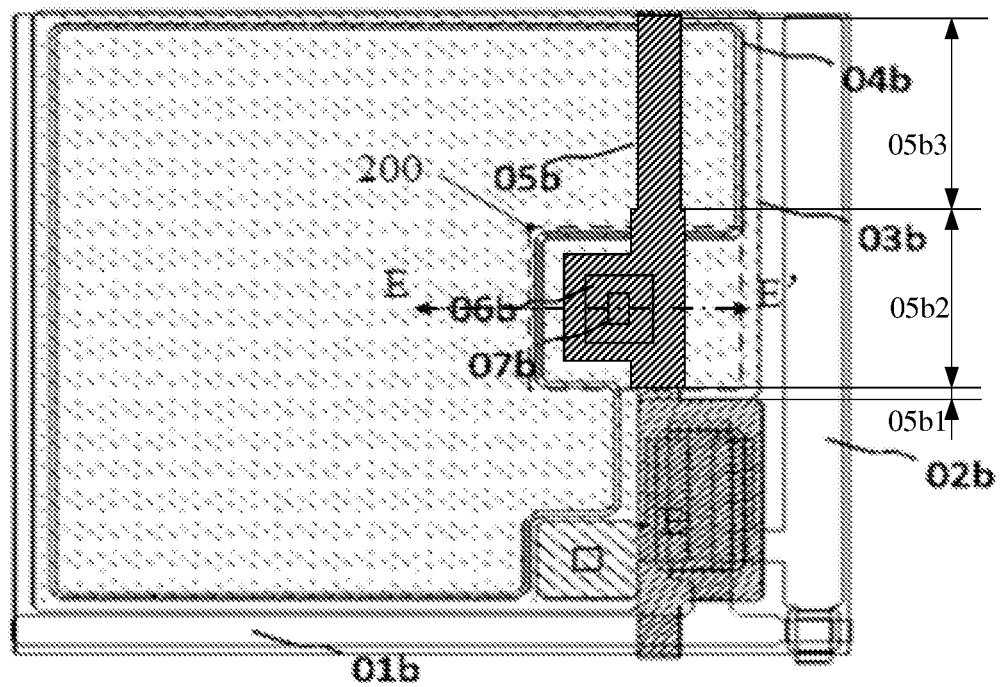
FIG. 9A is a plan view of a second alignment pixel unit of the flat panel detector provided by at least one embodiment of the present disclosure.
Figure 9B:
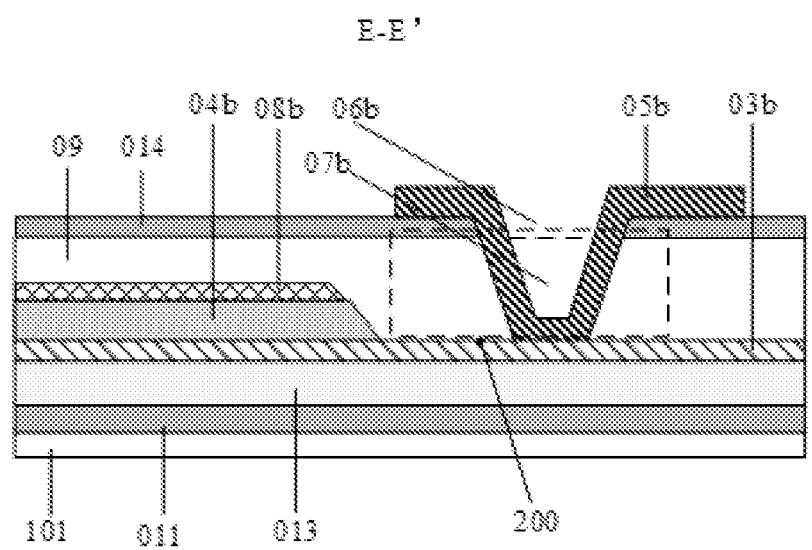
FIG. 9B is a schematic cross-sectional view along line E-E' in FIG. 9A.

FIG. 9A is a plan view of the second alignment pixel unit of the flat panel detector provided by an embodiment of the disclosure, and FIG. 9B is a schematic cross-sectional view along the line E-E' in FIG. 9A. Referring to FIG. 9A-FIG. 9B, each of at least part of the second alignment pixel units also includes the transistor and the photoelectric sensor. The structure of each second alignment pixel unit and the photosensitive pixel unit 1 illustrated in FIG. 5A-FIG. 5C has the following differences. Both the second electrode 08b and the photoelectric sensing layer 04b of the photoelectric sensor of the second alignment pixel unit have a hollow region 200, and the hollow region 200 exposes the first electrode 03b of the photoelectric sensor of the second alignment pixel unit. The bias voltage line 05b is electrically and directly connected with the first electrode 03b of the photoelectric sensor of the second alignment pixel unit through the second via hole 06b and the third via hole 07b, and the second via hole 06b and the third via hole 07b are communicated with each other to form a via hole. The second via hole 06b and the third via hole 07b expose the first electrode 03b of the photoelectric sensor, and the second via hole 06b and the third via hole 07b are located in the hollow region 200. In this way, the fixed bias voltage is provided to the first electrode 03b of the photoelectric sensor of the second alignment pixel unit through the bias voltage line 05b, so that the data line 02b reads the fixed voltage difference between the second electrode 08b and the first electrode 03b of the photoelectric sensor, so that the second alignment pixel unit has a fixed grayscale, thereby achieving that at least part of the second alignment pixel units are normally white pixel units. The gate line 01b in FIG. 9A is the same as the gate line 01 illustrated in FIG. 5A, and the data line 02b is the same as the data line 02 illustrated in FIG. 5A. For example, other unmentioned structures of the second alignment pixel unit, such as the semiconductor layer, the first electrode and the second electrode of the thin film transistor, and the like, are the same as those of the photosensitive pixel unit 1.

For example, the plane pattern of the hollow region 200 is an unclosed groove, that is, the second electrode 08b and the photoelectric sensing layer 04b of the photoelectric sensor respectively include the hollow region 200 and a non-hollow region partially surrounding the hollow region 200; the non-hollow region does not expose the first electrode 03b of the photoelectric sensor of the second alignment pixel unit. For example, as illustrated in FIG. 9A, the hollow region 200 is recessed inwardly from one side of the plane pattern of the second electrode 08b of the photoelectric sensor, and is recessed inwardly from one side of the plane pattern of the photoelectric sensing layer 04b of the photoelectric sensor. For example, in other embodiments, the plane pattern of the hollow region 200 is a closed pattern, that is, the second electrode 08b and the photoelectric sensing layer 04b of the photoelectric sensor respectively include a hollow region and a non-hollow region surrounding an entirety of the hollow region.

For example, as illustrated in FIG. 9A, the bias voltage line 05b includes a first portion 05b1, a second portion 05b2 and a third portion 05b3 connected in sequence along the extending direction of the bias voltage line 05b, and the line width of the second portion 05b2 is larger than the line width of the first portion 05b1 and larger than the line width of the third portion 05b3. In addition, the orthographic projection of the second portion 05b2 on the base substrate 101 overlaps with a part of the orthographic projection of the edge of the hollow region 200 on the base substrate 101. Due to the large step difference at the edge of the hollow region 200, that is, the edge of the second electrode 08b and the photoelectric sensing layer 04b surrounding the hollow region 200 have a height difference with respect to the first electrode 03b to form a slope, and the second portion 05b2 climbs the slope at the edge. Therefore, the line width of the second portion 05b2 is larger to avoid the risk of line breakage of the second portion 05b2 at the slope.

Figure 10A:
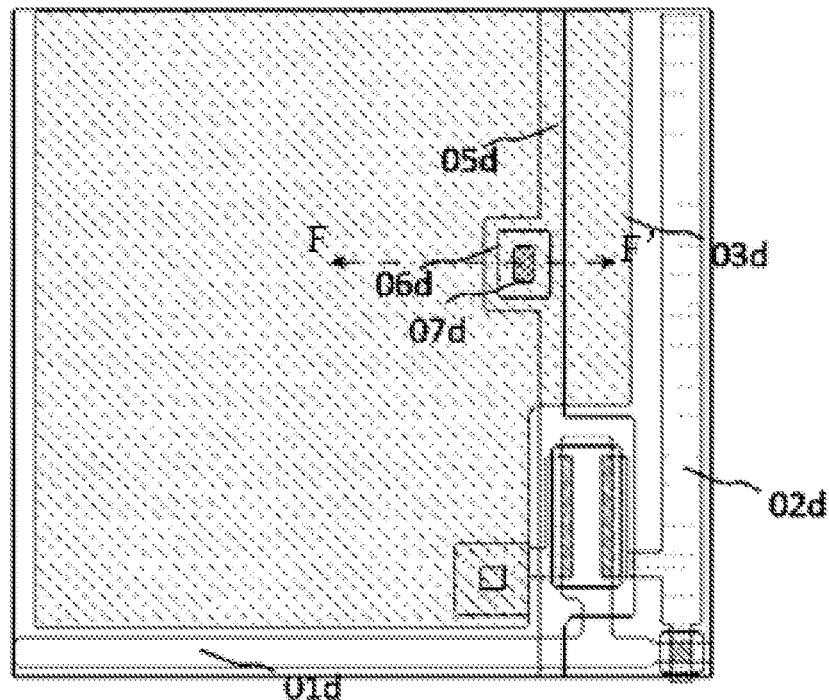
FIG. 10A is another plan view of the second alignment pixel unit of the flat panel detector provided by at least one embodiment of the present disclosure.
Figure 10B:
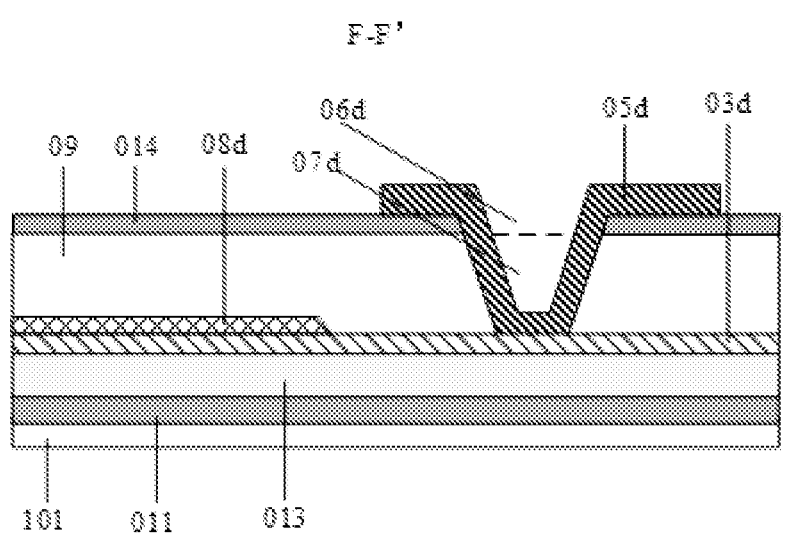
FIG. 10B is a schematic cross-sectional view along line F-F' in FIG. 10A.
Figure 10C:
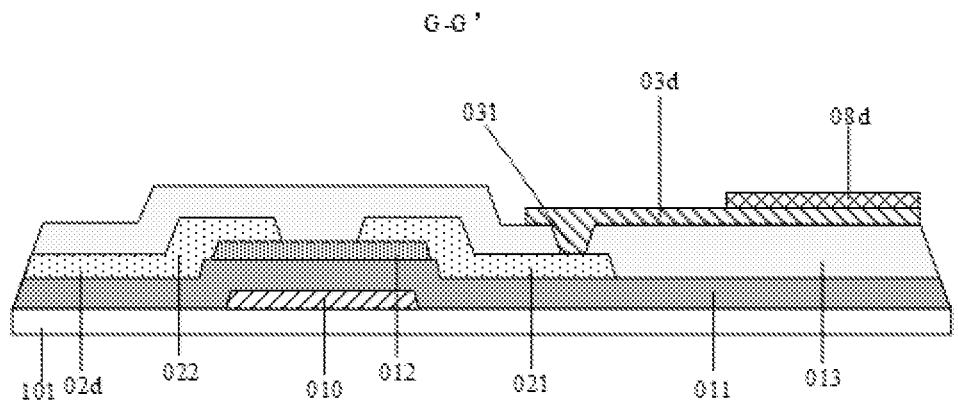
FIG. 10C is a schematic cross-sectional view along line G-G' in FIG. 10A.

FIG. 10A is another plan view of the second alignment pixel unit of the flat panel detector provided by an embodiment of the disclosure, FIG. 10B is a schematic cross-sectional view along the line F-F' in FIG. 10A, and FIG. 10C is a schematic cross-sectional view along the line G-G' in FIG. 10A. As illustrated in FIG. 10A-FIG. 10C, at least part of the plurality of second alignment pixel units each includes a third electrode 03d and a fourth electrode 08d and does not include a photoelectric sensing layer. The third electrode 03d is electrically connected with the bias voltage line 05d, and the third electrode 03d is electrically connected with the first electrode 021 of the transistor of the alignment pixel unit. The third electrode 03d and the fourth electrode 08d are stacked and in direct contact with each other so as to be electrically connected with each other. In this way, because there is no photoelectric sensing layer, the second alignment pixel unit does not generate an electrical signal that changes according to the change of the incident light. A fixed bias voltage is provided to the third electrode 03d through the bias voltage line 05d electrically connected with the third electrode 03d, and the third electrode 03d is electrically connected with the data line 02b through the thin film transistor, so that the electrical signal read by the data line 02b is basically the same as the fixed bias voltage, so that the second alignment pixel unit has a fixed grayscale, thereby achieving that the second alignment pixel unit is a normally white pixel unit. The gate line 01d in FIG. 10A is the same as the gate line 01 illustrated in FIG. 5A, and the data line 02d is the same as the data line 02 illustrated in FIG. 5A. For example, other unmentioned structures of the second alignment pixel unit, such as the semiconductor layer, the first electrode and the second electrode of the thin film transistor, and the like, are the same as those of the photosensitive pixel unit 1.

It should be noted that "the third electrode 03d is in direct contact with the fourth electrode 08d" means that there is no other layer or structure between the third electrode 03d and the fourth electrode 08d, the third electrode 03d and the fourth electrode 08d are not in contact with each other through via holes, and the surface of the third electrode 03d away from the base substrate 101 is in contact with the surface of the fourth electrode 08d close to the base substrate 101.

For example, the flat panel detector 10 further includes a coordinate acquisition unit and a data output unit. For example, the coordinate acquisition unit is a coordinate acquisition circuit. For example, the data output unit is a data output circuit. The coordinate acquisition unit is configured to acquire the coordinates of each alignment pixel unit or the coordinates of each alignment mark, and the real-time coordinates of at least part of the photosensitive pixel units for forming the charge image. The data output unit is configured to output an electrical signal of each photosensitive pixel unit for forming an image, and is configured to output the coordinates of each alignment pixel unit or each alignment mark and the real-time coordinates of at least part of the photosensitive pixel units for positioning the charge image so as to control the charge image to always be located in the image acquisition region. For example, for the purpose of convenient operation, a positioning point is selected on the charge image, and the position of the flat panel detector 10 is adjusted according to the positional relationship between the positioning point and the alignment pixel unit or alignment mark, and the flat panel detector 10 is movable so that the charge image is always located in the image acquisition region.

At least one embodiment of the present disclosure further provides an imaging system, and the imaging system includes any one of the flat panel detectors provided by the embodiments of the present disclosure, a position controller unit, a position adjuster device, and an imaging processor module. The position controller unit is configured to receive the coordinates of the plurality of alignment pixel units and the real-time coordinates of at least part of the photosensitive pixel units in real time, calculate a distance between the at least part of the photosensitive pixel units relative to the plurality of alignment pixel units by using the coordinates that are received, and send an instruction according to a calculation result. The position adjuster device is configured to receive the instruction from the position controller unit in real time, and adjust the position of the flat panel detector in real time under control of the instruction so that the charge image is always located in the image acquisition region. The imaging processor module includes a display and an imaging processor, and the display includes a preset display region. The imaging processor is configured to receive the electrical signal output by the flat panel detector and the position information of the charge image after adjusting the position of the flat panel detector, and generate the image of the object to be imaged in the preset display region by using the electrical signal and the position information of the charge image.

Figure 11:
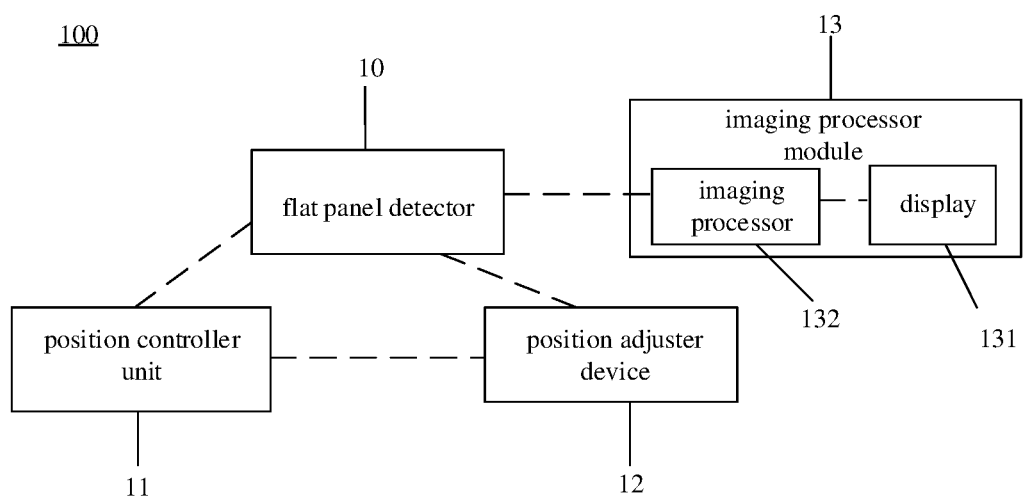
FIG. 11 is a schematic view of an imaging system provided by at least one embodiment of the present disclosure.

FIG. 11 is a schematic view of an imaging system provided by an embodiment of the disclosure. As illustrated in FIG. 11, the imaging system 100 includes any one of the flat panel detectors 10 provided by the embodiments of the present disclosure, and a position controller unit 11, a position adjuster device 12 and an imaging processor module 13. For example, the position controller unit 11 is a position controller circuit, the position adjuster device 12 is a position adjuster circuit, and the imaging processor module 13 is an imaging processor circuit. The position controller unit 11 is configured to receive the coordinates of the plurality of alignment pixel units and the real-time coordinates of the at least part of the photosensitive pixel units from the flat panel detector 10 in real time, calculate the distance of the at least part of the photosensitive pixel units relative to the plurality of alignment pixel units by using coordinates that are received, and send the instruction according to the calculation result. For example, the at least part of the photosensitive pixel units are used for generate the charge image under the action of the incident light, and are selected among the plurality of the photosensitive pixel units. The position adjuster device 12 is configured to receive the instruction from the position controller unit 11 in real time, and adjust the position of the flat panel detector 10 in real time under control of the instruction so that the charge image is always located in the image acquisition region D. The imaging processor module 13 includes a display 131 and an imaging processor 132. The display 131 includes a preset display region. The imaging processor 132 is configured to receive the electrical signal output by the flat panel detector 10 and the position information of the charge image after adjusting the position of the flat panel detector 10, and generate the image of the object to be imaged in the preset display region by using the electrical signal and the position information of the charge image.

For example, for the purpose of convenient operation, a positioning point is selected on the charge image, and the coordinates of the positioning point and the positional relationship between the positioning point and the alignment pixel unit or the alignment mark are obtained by the position controller unit 11. For example, the position controller unit 11 includes a processor, and the processor calculates the distance between the positioning point and the alignment pixel unit or the alignment mark. The position of the flat panel detector 10 is adjusted according to the distance, and the flat panel detector 10 moves to allow the charge image always in the image acquisition region.

For example, the imaging system 100 further includes a light emitter, which is configured to emit light to the object to be imaged, and the light irradiates the flat panel detector 10 after passing through the object to be imaged, and the light after passing through the object to be imaged is the above-mentioned incident light.

For example, the light emitter is further configured to rotate around the object to be imaged, and emit light to the object to be imaged at multiple angles so that corresponding charge images are generated at each angle in real time. The imaging processor module is configured to generate a three-dimensional image in the preset display region by processing the plurality of the charge images generated by emitting light to the object to be imaged at multiple angles.

For example, the imaging system 100 is used in the field of medical detection, where the light emitter emits X-ray. The imaging system 100 forms an image of parts (such as organs) of the human body using the X-ray. In this case, the imaging system 100 provided by the embodiments of the present disclosure forms the image of the object to be detected with ideal effect, for example, an ideal three-dimensional image is formed, which more truly and accurately reflects the morphology of the object to be detected, and thus obtains more real and accurate image information. Therefore, the accuracy of the detection result is improved, the imaging speed is improved, and the formed image is conveniently always located in the preset region of the display, the operation is simple, and the image output effect is good. For example, in still other embodiments, the light emitted by the light emitter is visible light, and a black and white image or a color image is formed. The black and white image or the color image is, for example, a plane image or a three-dimensional image. The application scenarios and imaging types of the flat panel detector provided by the embodiments of the present disclosure are not limited to the above situations.

The foregoing descriptions are merely exemplary implementations of the present disclosure, and are not used to limit the protection scope of the present disclosure, which is determined by the appended claims.

What is claimed is:

1. A flat panel detector, comprising a plurality of pixel units arranged in array, wherein
the plurality of pixel units comprises:
a plurality of photosensitive pixel units, wherein each of the plurality of photosensitive pixel units comprises a photoelectric sensor, and the photoelectric sensor is configured to convert an incident light into an electrical signal so that a photosensitive pixel unit in which the photoelectric sensor is located has a grayscale that changes according to a real-time change of the incident light; and
a plurality of alignment pixel units, wherein each of the plurality of alignment pixel units is configured to have a fixed grayscale, and the fixed grayscale does not change according to the real-time change of the incident light,
the plurality of alignment pixel units comprise: a plurality of first alignment pixel units, wherein each of the plurality of first alignment pixel units has a first fixed grayscale; and a plurality of second alignment pixel units, wherein each of the plurality of second alignment pixel units has a second fixed grayscale, and the first fixed grayscale is different from the second fixed grayscale.

2. The flat panel detector according to claim 1, wherein an absolute value of a difference between the first fixed grayscale and the second fixed grayscale is greater than or equal to 30% of an absolute value of a difference between a maximum grayscale and a minimum grayscale of the plurality of photosensitive pixel units.

3. The flat panel detector according to claim 2, wherein each of the plurality of first alignment pixel units is a normally black pixel unit, and each of the plurality of second alignment pixel units is a normally white pixel unit.

4. The flat panel detector according to claim 1, wherein at least two first alignment pixel units of the plurality of first alignment pixel units constitute a first alignment mark, and at least two second alignment pixel units of the plurality of second alignment pixel units constitute a second alignment mark.

5. The flat panel detector according to claim 4, wherein the first alignment mark and the second alignment mark are alternately arranged.

6. The flat panel detector according to claim 4, wherein
two first alignment pixel units of the plurality of first alignment pixel units constitute the first alignment mark, and the two first alignment pixel units located in the same first alignment mark are respectively located in adjacent columns and adjacent rows of the plurality of pixel units arranged in array; and
two second alignment pixel units of the plurality of second alignment pixel units constitute the second alignment mark, and the two second alignment pixel units located in the same second alignment mark are respectively located in adjacent columns and adjacent rows of the plurality of pixel units arranged in array.

7. The flat panel detector according to claim 4, wherein a total number of the at least two first alignment pixel units comprised in the first alignment mark is greater than a total number of the at least two second alignment pixel units comprised in the second alignment mark.

8. The flat panel detector according to claim 7, wherein
m*n first alignment pixel units of the plurality of first alignment pixel units constitute the first alignment mark, and m and n are both positive integers; and
two second alignment pixel units of the plurality of second alignment pixel units constitute the second alignment mark, the two second alignment pixel units located in the same second alignment mark are respectively located in adjacent columns and adjacent rows of the plurality of pixel units arranged in array.

9. The flat panel detector according to claim 4, comprising an image acquisition region, wherein
the image acquisition region is configured for acquiring image information and comprises at least part of photosensitive pixel units of the plurality of photosensitive pixel units; and the first alignment mark and the second alignment mark surround the image acquisition region, and a plurality of the first alignment marks and a plurality of the second alignment marks are evenly distributed in a circumferential direction of the image acquisition region.

10. The flat panel detector according to claim 1, wherein the photoelectric sensor comprises: a first electrode; a photoelectric sensing layer, stacked with the first electrode and configured to convert the incident light into the electrical signal, wherein the electrical signal is configured to control a real-time grayscale of the photosensitive pixel unit corresponding to the photoelectric sensor; and a second electrode, located on a side of the photoelectric sensing layer away from the first electrode;

each of the plurality of photosensitive pixel units and each of the plurality of alignment pixel units respectively comprise a transistor, comprising a gate electrode, a first electrode and a second electrode;

the flat panel detector further comprises signal lines, and the signal lines comprise:

a bias voltage line, electrically connected with the second electrode of the photoelectric sensor and configured to provide a bias voltage to each of the plurality of photosensitive pixel units;

a gate line, configured to provide a gate driving signal to the transistor; and a data line, intersecting the gate line to define the plurality of pixel units arranged in array, wherein in each of the plurality of photosensitive pixel units, the first electrode of the transistor is electrically connected with the first electrode of the photoelectric sensor, and the data line is electrically connected with the second electrode of the transistor to read the electrical signal generated by the photoelectric sensing layer.

11. The flat panel detector according to claim 10, wherein each of the plurality of first alignment pixel units also comprises the photoelectric sensor, the transistor of each of at least part of first alignment pixel units of the plurality of first alignment pixel units and the signal lines constitute an open circuit, so that the data line is incapable of reading the electrical signal generated by the photoelectric sensing layer and the at least part of first alignment pixel units are normally black pixel units.

12. The flat panel detector according to claim 11, wherein the gate electrode of the transistor of each of the at least part of first alignment pixel units of the plurality of first alignment pixel units is disconnected from the gate line.

13. The flat panel detector according to claim 11, wherein the second electrode of the transistor of each of the at least part of first alignment pixel units of the plurality of first alignment pixel units is disconnected from the data line.

14. The flat panel detector according to claim 11, wherein the first electrode of the transistor of each of the at least part of first alignment pixel units of the plurality of first alignment pixel units is disconnected from the first electrode of the photoelectric sensor.

15. The flat panel detector according to claim 10, wherein the bias voltage line is disconnected from the photoelectric sensor of each of the plurality of first alignment pixel units.

16. The flat panel detector according to claim 10, wherein at least part of second alignment pixel units of the plurality of second alignment pixel units each also comprise the photoelectric sensor;

the second electrode and the photoelectric sensing layer of the photoelectric sensor of each of the at least part of second alignment pixel units respectively have a hollow region, and the hollow region exposes the first electrode of the photoelectric sensor; and the bias voltage line is electrically connected with the first electrode of the photoelectric sensor through a first via hole, the first via hole exposes the first electrode of the photoelectric sensor, the first via hole is located in the hollow region, and the at least part of second alignment pixel units are normally white pixel units.

17. The flat panel detector according to claim 10, wherein at least part of second alignment pixel units of the plurality of second alignment pixel units each comprise a third electrode and a fourth electrode and does not comprise the photoelectric sensing layer;

the third electrode is electrically connected with the first electrode of the transistor of the second alignment pixel unit, and the fourth electrode is electrically connected with the bias voltage line; and the third electrode and the fourth electrode are stacked and in direct contact with each other so as to be electrically connected with each other, and the at least part of second alignment pixel units are normally white pixel units.

18. The flat panel detector according to claim 1, wherein the flat panel detector comprises an image acquisition region, the plurality of photosensitive pixel units generate a charge image according to the electrical signal; and the flat panel detector further comprises:

a coordinate acquisition unit, configured to acquire coordinates of the plurality of alignment pixel units and real-time coordinates of at least part of the photosensitive pixel units for forming the charge image; and a data output unit, configured to output the electrical signal of each of the plurality of photosensitive pixel units for forming the charge image, and configured to output the coordinates of the plurality of alignment pixel units and the real-time coordinates of the at least part of the photosensitive pixel units for positioning the charge image so as to control the charge image to always be located in the image acquisition region.

19. An imaging system, comprising:

the flat panel detector according to claim 18;

a position controller unit, configured to receive the coordinates of the plurality of alignment pixel units and the real-time coordinates of the at least part of the photosensitive pixel units in real time, calculate a distance of the at least part of the photosensitive pixel units relative to the plurality of alignment pixel units by using coordinates that are received, and send an instruction according to a calculation result;

a position adjuster device, configured to receive the instruction from the position controller unit in real time, and adjust a position of the flat panel detector in real time under control of the instruction so that the charge image is always located in the image acquisition region; and an imaging processor module, comprising a display and an imaging processor, wherein the display comprises a preset display region, and the imaging processor is configured to receive the electrical signal output by the flat panel detector and position information of the charge image after adjusting the position of the flat panel detector, and generate an image of an object to be imaged in the preset display region by using the electrical signal and the position information of the charge image.

20. The imaging system according to claim 19, further comprising:
a light emitter, configured to emit light to the object to be imaged, wherein the light irradiates the flat panel detector after passing through the object to be imaged,
the light emitter is further configured to rotate around the object to be imaged, and emit light to the object to be imaged at multiple angles to generate corresponding charge images at each angle in real time, and
the imaging processor module is configured to generate a three-dimensional image in the preset display region by processing a plurality of the charge images generated by emitting light to the object to be imaged at multiple angles.

* * * * *